United States Patent
Berndorfer et al.

(10) Patent No.: US 6,695,470 B1
(45) Date of Patent: Feb. 24, 2004

(54) APPARATUS AND METHOD FOR VISCOSITY MEASUREMENT

(75) Inventors: Axel H Berndorfer, Luxembourg (DE); Jim H Campbell, El Paso, TX (US); Amiyo K. Basu, Canton, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 10/238,482

(22) Filed: Sep. 10, 2002

(51) Int. Cl.[7] ............................................. G01N 11/00
(52) U.S. Cl. ........................ 374/45; 73/54.42; 374/54
(58) Field of Search ..................... 73/54.01, 54.02, 73/54.07, 54.42; 374/16, 43, 44, 159, 160, 45, 54, 102

(56) References Cited

U.S. PATENT DOCUMENTS

| | | | | |
|---|---|---|---|---|
| 3,930,399 A | * | 1/1976 | Munk | 73/54.42 |
| 3,977,234 A | * | 8/1976 | Lynch et al. | 73/54.01 |
| 4,426,878 A | * | 1/1984 | Price et al. | 73/54.07 |
| 4,466,275 A | * | 8/1984 | Thone | 73/54.16 |
| 4,578,988 A | | 4/1986 | Hori et al. | |
| 4,612,799 A | * | 9/1986 | Choi et al. | 73/54.36 |
| 4,733,556 A | | 3/1988 | Meitzler et al. | |
| 4,947,678 A | * | 8/1990 | Hori et al. | 73/54.42 |
| 5,044,764 A | * | 9/1991 | Aoki et al. | 374/16 |
| 5,167,144 A | * | 12/1992 | Schneider | 73/54.02 |
| 5,273,765 A | | 12/1993 | Weber et al. | |
| 5,289,716 A | * | 3/1994 | Schumacher | 73/54.19 |
| 5,341,672 A | | 8/1994 | Kawanami et al. | |
| 5,452,601 A | | 9/1995 | Hori et al. | |
| 5,750,887 A | | 5/1998 | Schricker | |
| 5,877,409 A | * | 3/1999 | Girling | 73/54.06 |
| 5,896,841 A | | 4/1999 | Nemoto et al. | |
| 5,905,196 A | * | 5/1999 | Parshall | 73/54.31 |
| 6,216,528 B1 | | 4/2001 | Carrell et al. | |
| 2001/0015095 A1 | * | 8/2001 | Konaka | 73/54.32 |
| 2003/0033859 A1 | * | 2/2003 | Schoeb et al. | 73/54.28 |

FOREIGN PATENT DOCUMENTS

GB        2259368 A   *  3/1993  ........... G01N/11/00

* cited by examiner

Primary Examiner—Diego F. F. Gutierrez
Assistant Examiner—Lydia M. De Jesús
(74) Attorney, Agent, or Firm—Jimmy L. Funke

(57) ABSTRACT

Apparatus and method for determining a change in the viscosity of a fluid, the apparatus including means for heating a portion of the fluid so that the heated portion will rise within the fluid, means for determining the heated portion's rise time, means for determining the heated portion's average velocity as it rises through the fluid and means for determining the viscosity of the fluid based on the rise time and/or average velocity of the heated portion. The method allows for permitting the temperature and agitation of the fluid to stabilize prior to heating a portion of the fluid so that it will rise within fluid. The rise time and/or average velocity of the heated portion is determined and the viscosity of the fluid may be determined the rise time and/or average velocity to a baseline rise time and/or average velocity. An output signal may be generated that is indicative of whether there has been a change in the fluid's viscosity and/or whether the fluid should be changed. The output signal may be sent to a display device such as that contained in the control panel of an automobile.

26 Claims, 2 Drawing Sheets

APPARATUS AND METHOD FOR VISCOSITY MEASUREMENT

BACKGROUND OF THE INVENTION

This invention relates generally to measuring viscosity and more particularly to a method and apparatus for measuring the change in viscosity of a fluid as the condition of the fluid deteriorates.

Hydraulic oil such as lubricating oil for an internal combustion engine inevitably experiences changes in its viscosity over time as a function of oil grade, temperature, state of deterioration and other operational parameters. Oil viscosity is an important property because it defines the oil film thickness between moving parts of an engine. It also affects cold crank capability, fuel consumption and for some engines it influences the ability to control emissions such as in a diesel injection system with a hydraulic booster. Oil viscosity may also be used to determine the end of the oil's useful life. For example, a predetermined threshold value of oil viscosity may be used alone or in conjunction with other oil properties such as oil acidity, particle count, content of certain additives and level of contamination to signify that a volume of oil has reached the end of its useful life and needs to be replaced or reconditioned.

The necessity of changing oil in an internal combustion system such as an automobile is typically determined based on recommendations made by the manufacturer and found in the vehicle's owner's manual. Such recommendations are based on assumptions that may or may not apply to a particular user's specific environmental and/or driving conditions. Changing oil based on the manufacturer's recommendations may be satisfactory in many circumstances. However, if an inferior grade of oil is used or an engine is operated in a harsh environment the proper interval for oil change may vary as a function of predetermined oil condition parameters, one of which may be viscosity. Consequently, the ability to oil viscosity quickly and accurately may be useful to avoid damage to an engine.

One known method for determining viscosity employs an arrangement that purportedly measures the viscosity of a fluid by determining the time required for a standard element to travel a predetermined distance through the fluid. This arrangement is not capable of in-situ measurements of oil viscosity, which may be desirable in many applications such as in the automobile industry. Other devices and methods are known for measuring viscosity that require samples of the liquid in question to be taken to a laboratory of other facility for analysis. These techniques are not suitable for in-situ measurements.

BRIEF SUMMARY OF THE INVENTION

One exemplary embodiment of the present invention provides an in-situ method and apparatus for measuring the change in viscosity of a lubricant as the quality of the lubricant deteriorates during operational use. One aspect of the present invention allows for the correlation of the heat convection properties of the lubricant to the lubricant's viscosity. A heating means may be provided for locally increasing the lubricant's temperature. At least a portion of the heated lubricant may then rise within the bulk lubricant volume due to the heated portion's reduced density. An operational rise time may then be determined, which may be determined after a vehicle is shut down, for example, to determine the necessity of changing or treating the bulk lubricant. The operational rise time may be the difference between the actuation of a heat pulse from the heating means to heat a portion of the bulk lubricant and the arrival of the heated portion at a predetermined distance from the heating means. The operational rise time may then be used to determine the bulk fluid's viscosity.

An alternate embodiment allows for the operational rise time to be the amount of time it takes the heated portion to rise from a position proximate the point at which it is heated to a position proximate a second point that is a known distance from the first point. Yet another alternate embodiment allows for determining the heated portion's average velocity, which may be determined as a function of the temperature difference between the heated lubricant portion and the rest of the bulk lubricant volume. The average velocity may also be a function of shear forces within the lubricant, which are determined by the lubricant's viscosity.

One aspect of the present invention allows for creating a set of look up tables containing baseline rise times at a known temperature for a set of bulk fluids having a known viscosity. The operational rise time may then be compared to the appropriate baseline rise time contained in the look up table to determine the viscosity change of the bulk lubricant. The baseline rise time data may be interpolated to determine qualitative and/or quantitative information regarding the viscosity of the bulk lubricant in response to determining the operational rise time. This information may then be used to determine whether the bulk lubricant needs to be changed or treated.

One embodiment of the present invention allows for a temperature sensor to take a first temperature at a predetermined height to establish a baseline temperature of the bulk lubricant at that height. The heating means may heat a portion of the bulk lubricant at a predetermined point below the predetermined height. The amount of time it takes the heated portion to rise from the heating means to the predetermined height may be measured by determining when the temperature change occurs at the predetermined height. A change, if any, in the viscosity of the fluid may then be determined.

Another aspect of an exemplary embodiment of the present invention allows for at least one temperature sensor to be used in a quantity of bulk oil for measuring a temperature as a quantity of heated lubricant passes a known point. In an alternate embodiment two temperature sensors may be used to measure temperature change between a first point and a second point in the bulk oil as the heated oil passes between those points.

DETAILED DESCRIPTION OF THE INVENTION

Figure 1:
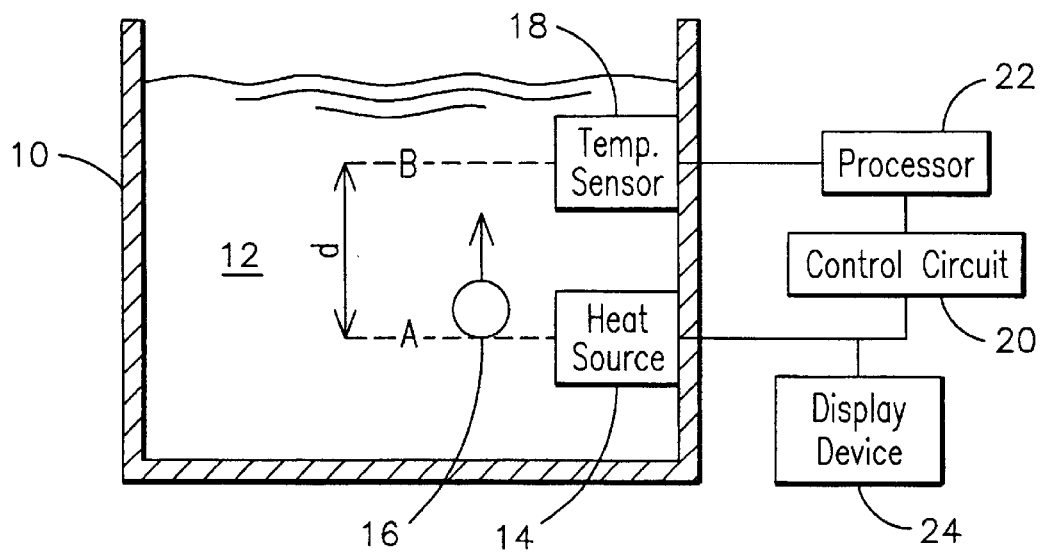
FIG. 1 illustrates a cross section of a container for holding a fluid with an exemplary embodiment of the present invention contained therein.

FIG. 1 illustrates a cross section of a container 10 for holding a quantity of bulk fluid 12 such as petroleum-based oil used as a lubricant for lubricating and cooling moving components of the internal combustion engine of an automobile, for example. A heating means 14 may be provided to locally heat a portion 16 of the bulk fluid 12. The heating means 14 may be a conventional heat source such as a smart heating source, for example, adapted to control voltage and current. In alternate embodiments the heating means 14 may be other conventional devices such as radiative, resistive, and inductive heaters, for example. A temperature sensor 18 may be provided to measure a change in temperature at a predetermined point above the heating means 14. The temperature sensor 18 may be a conventional device such as a resistive thermal device ("RTD"), thermocouple, thermometer or other devices known in the art. The heated portion 16 of bulk fluid 12 will rise after being heated due to its lower density relative to the bulk fluid 12. One exemplary embodiment of the present invention allows for correlating the amount of time it takes the heated portion 16 to travel a known distance through the bulk fluid 12 with viscosity in order to measure a change in viscosity of the bulk fluid 12. The heated portion 16 may cool as it rises in the bulk fluid 12 due to the thermal conductivity of the bulk fluid 12 and the heated portion 16. However, the thermal conductivity of petroleum-based lubricants such as those used in automobiles, for example, are substantially equal and whatever effect thermal conductivity has on the heated portion 16 is substantially the same among the lubricants. Other embodiments of the present invention may take into account differences in thermal conductivity among bulk fluids to the extent the differences impact the determination of viscosity changes in those fluids.

The temperature sensor 18 may be used to detect a change in temperature of the bulk fluid 12 at a predetermined point or height B above the heating means 14. After heating, the velocity of the portion of heated fluid 16 when moving distance d between points A and B is a function of at least: a) the temperature difference between the bulk fluid 12 and the heated portion 16, and b) the viscosity of the bulk fluid 12. In one exemplary embodiment the distance d may be between about one (1) to two (2) centimeters and the temperature difference between the bulk fluid 12 and the heated portion 16 may be about 5 degrees Celsius. Distance d and the temperature difference between the heated portion 16 and the bulk fluid 12 may vary in alternate embodiments of the present invention depending on specific design, performance and other parameters. For instance, the temperature difference between the heated portion 16 and the bulk fluid 12 may be a function of the duration of a heat pulse generated by the heating means 14. The longer the heat pulse the greater the temperature differential. It is desirable to provide a heat pulse that results in a sufficiently stable or defined heated portion 16. This allows for the heated portion 16 to travel through the predetermined distance without diffusing too much into the bulk liquid 12 or otherwise having its physical properties degrade before it reaches the temperature sensor 18, for example. Similarly, if the heated portion 16 is not sufficiently heated it may not travel to the temperature sensor 18 with sufficient characteristics for the sensor 18 to detect a temperature change. It has been determined by the assignee of the present invention through empirical testing that providing a heat pulse generally between about 0.5 and 1.0 seconds allows for the heated portion 16 to travel an appropriate distance to have its operational rise time determined. Alternate embodiments may provide for a heat pulse of greater or lesser values depending at design parameters of the viscosity sensor. For example, in one exemplary embodiment the heat pulse may be as short as about 0.10 seconds. Thus, it will be appreciated that the present invention is not limited to any specific time duration for heating portion 16.

One aspect of the present invention allows for determining the operational rise time of the heated portion 16. In one exemplary embodiment the operational rise time may be defined as the time difference between the time a heat pulse from heating means 14 is actuated and the time the heated portion 16 "arrives", or is initially detected, at a point a known distance away such as point B proximate the temperature sensor 18. The temperature sensor 18 may detect a localized change in temperature of the bulk fluid 12 that is indicative of the "arrival" of the heated portion 16. As the heated portion 16 rises toward height B the temperature sensor 18 will detect a temperature change in the bulk liquid 12 proximate the temperature sensor 18. This is due to the heated portion 16 rising sufficiently close to the temperature sensor 18 so that the sensor may measure a local change in temperature of the bulk fluid 12. In an alternate embodiment, the "arrival" of the heated portion 16 may be detected by a laser diode that detects a change in the index of refraction of the heated portion 16 as it passes near the sensing area. The temperature sensor 18 may be configured to send a data signal to a processor 22 that the heated portion 16 has been detected. The processor 22 may then calculate the operational rise time and/or the average velocity of the heated portion 16. The operational rise time may then be compared to a baseline rise time for that bulk fluid 12 via a lookup table stored in a database accessible by the processor 22, for example. The baseline rise time may be determined for the bulk fluid 12 at a selected temperature when the bulk fluid's 12 viscosity is known such as before the bulk fluid 12 is subjected to operating conditions in container 10. In alternate embodiments the operational rise time of the heated portion 16 may be calculated over a different distance d, such as the time it takes the heated portion 16 to move between any two known points, provided that the baseline rise time is calculated using the same points. Thus, measuring changes in temperature over a distance d should not be construed as a limitation of the present invention. The assignee of the present invention has determined through empirical experimentation that the difference between the baseline and operating rise times is indicative of a change in viscosity of the bulk fluid 12. The viscosity of the surrounding bulk liquid 12 will affect the rise rate of the heated portion 16. The greater the viscosity of the surrounding bulk fluid 12 the more slowly the heated portion 16 will rise.

A control circuit 20 and the processor 22 may be provided for data analysis and as means for controlling the temperature sensor 18, heat source 14 and/or a display device 24. The control circuit 20 and processor 22 may be separate components or they may be combined into one unit as will be recognized by those skilled in the art. Processor 22 may be configured with appropriate software to calculate the difference between the baseline rise time and the operational rise time for a selected bulk fluid 12. The difference may then be used to determine whether that bulk fluid 12 has experienced a change in its viscosity. The processor 22 may be programmed to express a change in viscosity in qualitative and/or quantitative terms. An electronic data signal indicative of any change in the viscosity of the bulk liquid 12 may be generated by the processor 22 and sent to a display device 24, for example, by the control circuit 20. One aspect of the present invention allows for selecting a set of criteria for determining whether the processor 22 will send a signal to the display device 24, for example, and what information that signal will contain. For example, the set of criteria may include a variety of variables such as a predetermined percentage change in the viscosity of the bulk fluid 12. If the percentage change in the viscosity of the bulk fluid 12 from the baseline viscosity or previous viscosity reading is equal to or greater than twenty percent (20%) then the data signal may cause the display device 24 to indicate that it's time to change the bulk fluid 12. Alternate embodiments may include other variables such as recommendations from an automobile manufacturer for changing the automobile's oil based on environmental conditions, oil conditions, viscosity changes, etc. In one exemplary embodiment of the present invention the display device 24 may be part of the control panel of an automobile and may indicate to the driver, based on predetermined conditions, that the motor oil, for example, needs to be changed soon or that it needs to be changed as immediately as possible. It will be recognized by those skilled in the art that the display device 24 may be a variety of other types of devices that may be stand alone devices or integrated with other devices.

Figure 2:
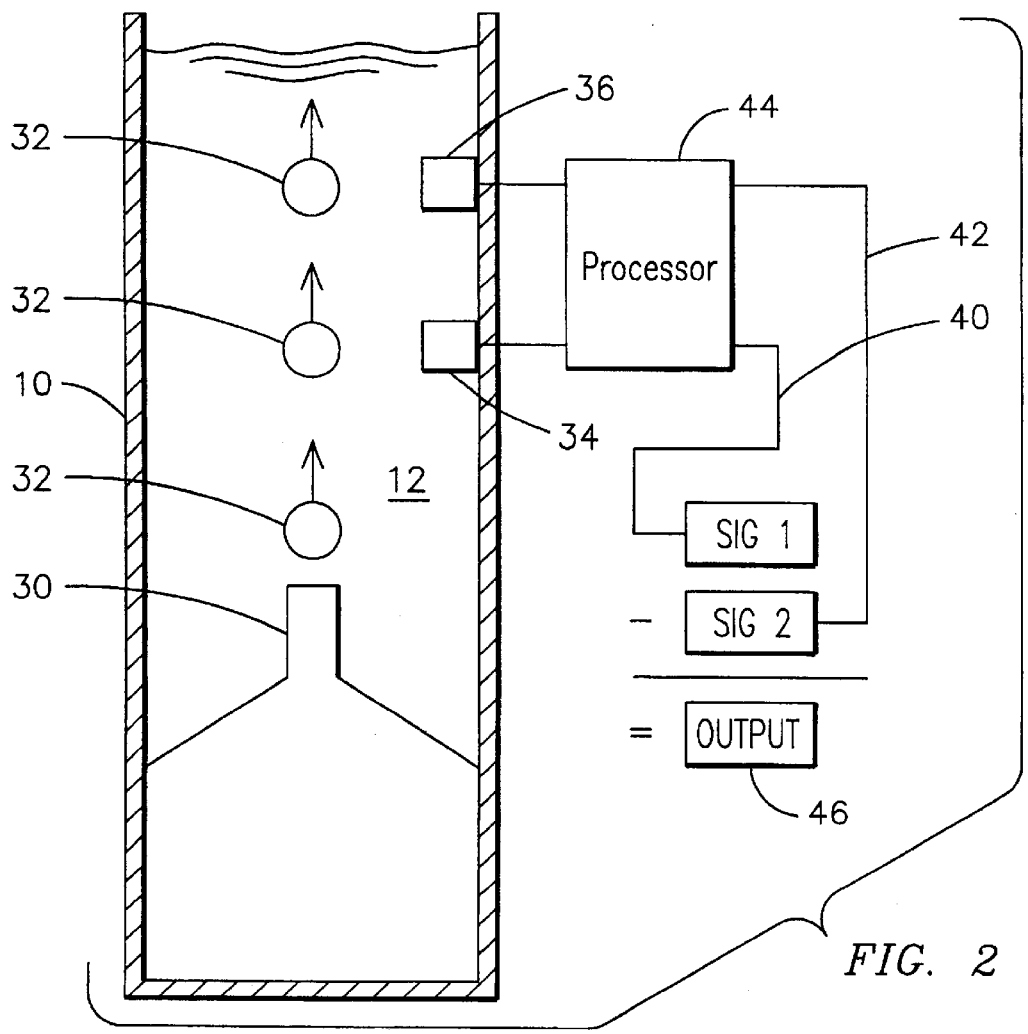
FIG. 2 illustrates a cross section of a container for holding a fluid with another exemplary embodiment of the present invention contained therein.

FIG. 2 shows another exemplary embodiment of an apparatus in accordance with another aspect of the present invention. A container 10 similar to the one shown in FIG. 1 may hold a quantity of bulk liquid 12 such as the motor oil of an automobile, for example. In one exemplary embodiment the container 10 may be the oil pan of an automobile but it will be recognized by those skilled in the art that container 10 may comprise a wide range of other types of containers used for other purposes. A heating means may be provided, such as heat source 30, situated near the bottom of the container 10 to heat a portion of the bulk liquid 12. Heat source 30 may be any conventional heat source such as a glow plug, or other resistive heaters, as well as inductive, conductive, or radiative heaters connected to a power supply, for example. The heated portion 32 of bulk liquid 12 will rise within the bulk liquid 12 due to its lower density relative to the bulk liquid 12. A first temperature sensor 34 and a second temperature sensor 36 may be provided in spaced relation within the bulk liquid 12. Sensors 34 and 36 may be conventional heat sensors such as a resistive thermal device, thermocouple, thermometer or other such device. In one exemplary embodiment each of the sensors 34 and 36 may be a resistive thermal device ("RTD") configured to generate an output signal in response to changes in resistance. For example, sensor 34 may generate a first output signal 40 and the sensor 36 may generate a second output signal 42. The output signals 40 and 42 may change in response to changes in the resistance of each sensor 34 and 36 as the heated portion 32 moves past each sensor's respective position within the bulk liquid 12. In this respect, each sensor 34 and 36 exhibits increasing resistance as the temperature of the bulk liquid 12 near them increases. A signal processor 44 may be provided to amplify the first and second output signals 40 and 42 and calculate an output signal 46 by subtracting the second output signal 42 from the first output signal 40. As shown in FIG. 2, the heated portion 32 is shown in different positions as it rises within the bulk liquid 12. The heated portion 32 may rise so that it passes the first sensor 34 and the second sensor 36. As the heated portion 32 first approaches and then passes first sensor 34, the first output signal 40 may change in response to the higher temperature of the heated portion 32. Similarly, as the heated portion 32 approaches and passes the second sensor 36, the second output signal 42 may change in response to the higher temperature of the heated portion 32. The output 46 may be used by the processor 44 to calculate the operational rise time of the heated portion 32. The operational rise time may be calculated by the processor 22 and be defined as the time it takes the heated portion 32 to travel between the sensors 34 and 36. As suggested above, other embodiments may calculate the operating rise time using different reference points provided that the operating rise time may be compared to a corresponding lookup table to determine a change in viscosity of the bulk fluid 12.

In an alternate embodiment, the velocity, average velocity and/or acceleration of the heated portion 32 may be determined in the region of the temperature sensors 34 and 36, for example. Empirical testing conducted by the assignee of the present invention has demonstrated that the velocity, average velocity and operating rise time of the heated portion 32 is directly or monotonically related to the viscosity of the bulk liquid 12. This is true for any heated portion 16, 32 and 53 illustrated in the Figures. That is, the movement of a heated portion through the bulk fluid 12 is a function of the bulk fluid's 12 viscosity. The velocity or average velocity increase in response to a decrease in the viscosity of bulk fluid 12. Similarly, the operating rise time decreases in response to the viscosity of the bulk fluid 12 decreasing. Measuring the velocity, average velocity and/or operating rise time of a heated portion 16, 32 or 53 allows for a qualitative and/or quantitative measurement of the bulk liquid's 12 viscosity to be determined by comparing those measurements to a corresponding lookup table or tables and making appropriate interpolations.

Figure 3:
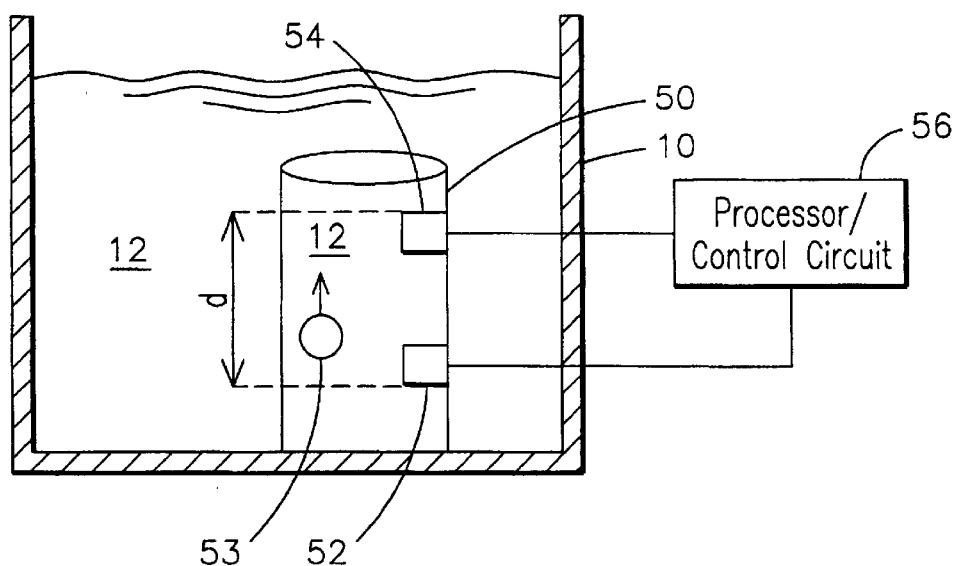
FIG. 3 illustrates a cross section of a container for holding a fluid with another exemplary embodiment of the present invention contained therein.

Another exemplary embodiment of the present invention is shown in FIG. 3, which illustrates a substantially cylindrical tube 50 submersed within the bulk liquid 12 that may act as a housing or means for shielding the heated portion from crosscurrents. In alternate embodiments, the tube 50 may be other shapes such as rectangular, oval, square, polygonal, etc. provided that the heated portion of the bulk fluid 12 is substantially shielded from crosscurrents in the fluid 12. Tube 50 may be submersed so that it contains a portion of the bulk liquid 12 and may be made of conventional materials such as high temperature metal, ceramic, or plastic, for example. The bulk liquid 12 may be contained within the container 10, which may be the oil pan of an automobile, for example. In one exemplary embodiment the tube 50 may be attached to a base (not shown) of a sensing apparatus, having a variety of sensing means, with the base affixed to the exterior of an automobile's oil pan, for example. In this respect, the tube 50 may extend upright into the bulk liquid 12 contained within the oil pan. In alternate embodiments, the tube 50 may be affixed directly within container 10. Heating means 52, such as the heat source 14 of FIG. 1 and the heat source 30 of FIG. 2, may be provided as means to heat a portion 53 of the bulk liquid 12. Temperature sensing means 54, such as the temperature sensor 18 of FIG. 1 and the sensors 34 and 36 of FIG. 2, may be provided as means for detecting a change in temperature of the bulk liquid 12 proximate the sensing means 54. A processor and control circuit 56 may be provided to control the temperature sensing means 54 and the heating means 52 and to calculate the velocity, average velocity and/or operational rise time of the heated portion 52 as it travels distance d shown in FIG. 3. In one exemplary embodiment distance d may be between about one (1) and ten (10) centimeters but may be other distances as a function of design parameters. Those skilled in the art will recognize that distance d may vary with at least the size of container 10 and tube 50 as well as the properties, including viscosity, of the bulk liquid 12. One advantage of providing tube 50 is that it may reduce or eliminate crosscurrents in the bulk liquid 12. This may be desirable because crosscurrents in the bulk liquid 12 may disrupt the flow or upward motion of the heated portion 32 causing less accurate calculations of the bulk liquid's 12 viscosity. Tube 50 may range in its size as a function of design parameters. Capillary forces should be taken into account for tube's 50 having small diameters. That is, any resistance to the heated portion's 53 ability to rise within the tube 50 should be derived from the bulk fluid 12 and not due to the geometry of tube 50. In one exemplary embodiment tube 50 may have a length of approximately one (1) centimeter but other lengths will be recognized by those skilled in the art. It has been determined by the assignee of the present invention that as the path length of tube 50 decreases, the energizing time for a heat pulse generated by heating means 52 should be reduced, with a correspondingly smaller temperature rise in the heated portion 53. This is to prevent the size of heated portion 53, for example, from becoming too large relative to the distance portion 53 needs to travel.

Figure 4:
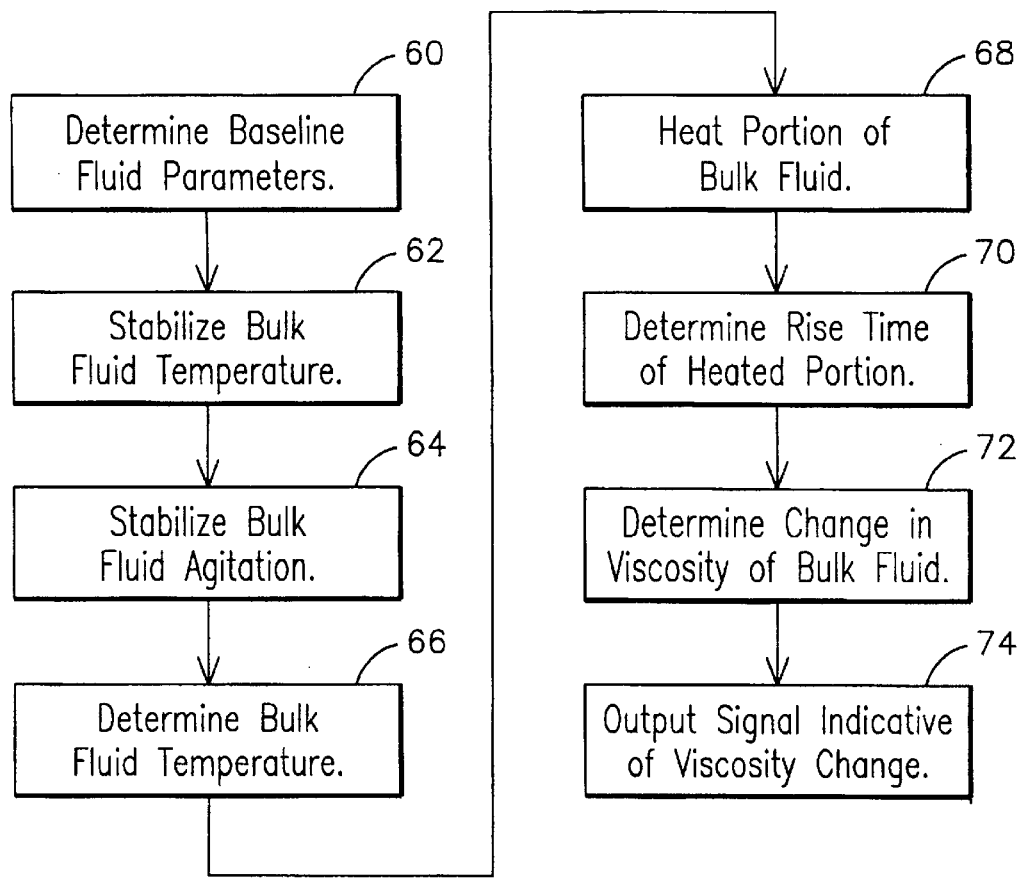
FIG. 4 is a flow diagram of an exemplary method in accordance with one aspect of the present invention.

FIG. 4 is a flow chart of an exemplary embodiment of a method for measuring viscosity in accordance with one aspect of the present invention. Step 60 allows for establishing or determining a set of baseline parameters associated with a fluid such as the lubricant or oil used in an internal combustion engine of an automobile, for example. Baseline parameters may include the fluid's viscosity, additives content, thermal conductivity, SAE rating and other parameters associated with the fluid. One aspect of the present invention allows for establishing a baseline rise time at a predetermined temperature for a lubricant or a range of lubricants. Determining baseline parameters allows for changes in the parameters to be determined based on use of the bulk fluid 12, for example. Certain changes may indicate that the bulk fluid 12 needs to be replenished or replaced due to the associated parameter deviating too much from their its respective baseline. For example, oil used in an automobile may need to be replaced if the oil's viscosity becomes too low compared to its respective baseline viscosity and/or if the oil experiences a step change or large decrease in its viscosity from one viscosity measurement to the next.

Step 62 allows for the temperature of the bulk fluid 12 to stabilize prior to determining whether there has been a change in its viscosity. This is to ensure that movement of a heated portion is essentially caused by its being heated by a heating means such as 14 or 34. One exemplary embodiment allows for the bulk fluid's 12 temperature to stabilize by waiting a predetermined period of time after an automobile's engine is shutdown, for example, before heating a portion of the bulk liquid in step 68. This allows the temperature of the bulk fluid 12 to achieve equilibrium with the ambient temperature. Step 64 allows for the agitation of bulk fluid 12 to stabilize to allow a heated portion of the bulk fluid 12 to rise within the bulk fluid 12 in a non-volatile fluid environment. For example, during the operation of an automobile, motor oil is distributed to moving parts and collects in an oil pan for re-circulation. When the engine is shutdown, the oil collects in the oil pan and stabilizes so that it is not agitating. Step 64, in one exemplary embodiment, allows for waiting a predetermined period of time after an automobile's engine is shutdown prior to heating a portion of the bulk fluid 12 to determine a change in its viscosity.

Another aspect of the method illustrated in FIG. 4 allows for the temperature of the bulk fluid 12 to be determined in step 66. This allows for determining changes in the bulk fluid's 12 viscosity at more than one temperature. Thus, one could make, if desired, another determination of viscosity after the bulk fluid's 12 temperature and agitation have stabilized. Accordingly, one aspect of the present invention allows for determining changes in viscosity, for example, at two (2) discrete bulk fluid 12 temperatures after engine shutdown of an automobile. A first measurement may be taken when the bulk fluid's 12 temperature is approximately 100 degrees Celsius and a second measurement at approximately 40 degrees Celsius, for example. Because viscosity is temperature dependent, this allows for developing a viscosity profile of the bulk fluid 12 at different temperatures that may be used to determine whether the oil in an automobile, for example, needs to be changed. Alternate embodiments may measure viscosity at more than two temperatures. To determine whether there has been a change in the viscosity of the bulk fluid 12, step 68 allows for heating a portion of the bulk fluid 12 so that the heated portion will rise within the bulk fluid 12. Step 70 allows for determining the operational rise time of the heated portion as described above. The operational rise time of the heated portion may be used to determine whether there has been a change in the viscosity of the bulk fluid 12 in step 72. Alternate embodiments may use the velocity and/or average velocity of the heated portion to determine a change in viscosity of the bulk fluid 12. Step 74 allows for an output signal to be generated, such as by processor 22 (FIG. 1), indicative of a change in the viscosity of bulk fluid 12. The output signal may be sent to a display device such as one found in the control panel of an automobile, for example. The output signal may be based on a set of criteria, such as the bulk fluid 12 experiencing a twenty percent (20%) change in viscosity for example, that, if met, will cause the display device to display a specific message. The message may be that the bulk fluid 12 needs to be changed as soon as possible or that it needs to be changed soon, for example.

While the exemplary embodiments of the present invention have been shown and described by way of example only, numerous variations, changes and substitutions will occur to those of skill in the art without departing from the invention herein. Accordingly, it is intended that the invention be limited only by the spirit and scope of the appended claims.

We claim:

1. An apparatus for determining a change in the viscosity of a fluid, the apparatus comprising:

means for heating a portion of the fluid so that the heated portion will rise within the fluid;

means for determining an operational rise time of the heated portion; means for determining a value correlating to the determined operational rise time; and means for comparing the value correlating to a value correlating to operational rise time to a value correlating to a baseline rise time to determine the change in viscosity of the fluid.

2. The apparatus of claim 1, wherein in said means for comparing, the value correlating to the determined rise time is an average velocity of the heated portion and the value correlating to a baseline rise time is a baseline average velocity.

3. The apparatus of claim 1 further comprising:

a container for holding a quantity of the fluid.

4. The apparatus of claim 3 further comprising:

means for shielding the heated portion of the fluid from crosscurrents in the fluid, the means for shielding disposed within the container.

5. The apparatus of claim 1 further comprising:

means for shielding the heated portion of the fluid from crosscurrents in the fluid, the means for shielding disposed within the container.

6. The apparatus of claim 1, the means for determining the operational rise time comprising:

a temperature sensor disposed a known distance above the heating means such that the heated portion of fluid will rise from the heating means toward the temperature sensor;

a control circuit for controlling the heating means and the temperature sensor;

a processing module configured to calculate a difference between a first time when a heat pulse is generated by the heating means and a second time when the heated portion is sensed by the temperature sensor, said difference corresponding to the operational rise time.

7. The apparatus of claim 6 further comprising:

a display, device for receiving a data signal from the processing module, the data signal indicative of whether the fluid needs to be changed.

8. The apparatus of claim 1, the means for determining the operational rise time comprising:

a first temperature sensor;

a second temperature sensor disposed a known distance above the first temperature sensor;

a control circuit for controlling the heating means, the first temperature sensor and the second temperature sensor; and a processing module configured to calculate an amount of time for the heated portion to rise from the first temperature sensor to the second temperature sensor, said amount of time corresponding to the operational rise time.

9. The apparatus of claim 1 wherein the means for heating generates a heat pulse for a predetermined amount of time.

10. The apparatus of claim 9 wherein the predetermined amount of time is between about 0.1 and 1.0 seconds.

11. The apparatus of claim 1 further comprising:

means for determining a relative viscosity of the fluid based on an average velocity of the heated portion;

means for determining an absolute viscosity of the fluid based on a correlation of the operational rise time of the heated portion to an operational rise-time of heated portions of fluids having known viscosity; and means for determining the absolute viscosity of the fluid based on a correlation of an average velocity of the heated portion to an average velocity of the heated portions of fluids having known viscosity.

12. An apparatus for measuring a change in the viscosity of a fluid in an internal combustion engine, the apparatus comprising:

a heat source disposed within the fluid for heating a portion of the fluid so that the portion of the fluid will rise within the fluid;

a first sensor disposed within the fluid a known distance above the heat source for sensing the heated portion of the fluid;

a control circuit for activating the heat source to generate a heat pulse to heat the portion of the fluid and for controlling the first sensor; and a processing module configured to calculate an operational rise time of the heated portion of the fluid and to compare the operational rise time to a baseline rise time to determine a change in the viscosity of the fluid.

13. The apparatus of claim 12 wherein the first sensor is a temperature sensor.

14. The apparatus of claim 12 wherein the operational rise time is calculated by taking the difference between a first time when the heat source generates a heat pulse and a second time when the heated portion is detected by the first sensor.

15. The apparatus of claim 12 further comprising:

a second sensor disposed a known distance above the first sensor wherein the operational rise time is calculated by taking the difference between a first time when the heated portion is detected by the first sensor and a second time when the heated portion is detected by the second sensor.

16. The apparatus of claim 15 wherein the second sensor is a temperature sensor.

17. The apparatus of claim 12 further comprising:

a housing for shielding the heated portion of the fluid from crosscurrents in the fluid.

18. The apparatus of claim 12 further comprising:

a display device for receiving data from the processing module, the data being indicative of whether the fluid needs to be changed.

19. A method for determining a change in the viscosity of a lubricating oil used in an internal combustion engine of a vehicle, the internal combustion engine having a sump for collecting the lubricating oil when the engine is shutdown, the method comprising:

affixing a container to the sump so that the container is positioned within the sump to be filled with the lubricating oil;

heating a portion of the lubricating oil so that the heated portion will rise within the container;

calculating a first operational rise time of the heated portion; and comparing the first operational rise time to a baseline rise time to determine the change in the viscosity of the lubrication oil.

20. The method of claim 19 further comprising:

shielding the heated portion from crosscurrents within the lubricating oil.

21. The method of claim 19 further comprising:

providing a processing module for calculating the first operational rise time of the heated portion and comparing the first operational rise time to the baseline rise time to determine the change in the viscosity of the lubrication oil;

determining whether the lubricating oil in the sump needs to be changed; and sending a data signal to a display device indicative of whether the lubricating oil in the sump needs to be changed.

22. The method of claim 21 further comprising:

indicating that the lubricating oil in the sump needs to be changed if the change in the viscosity of the lubricating oil is equal to or greater than twenty percent.

23. The method of claim 22 further comprising:

indicating that the lubricating oil in the sump needs to be changed based on a set of manufacturer's specifications.

24. The method of claim 19 wherein the steps of calculating and comparing are performed within a predetermined period of time after the engine is shutdown.

25. The method of claim 19 further comprising:

calculating a second operational rise time of the heated portion; and comparing the second operational rise time to a second baseline rise time to determine the change in the viscosity of the lubricating oil.

26. The method of claim 25 wherein:

the step of calculating the first operational rise time is performed at a first temperature of the lubricating oil; and the step of calculating the second operational rise time is performed at a second temperature of the lubricating oil.

* * * * *